United States Patent
Schabert et al.

(10) Patent No.: US 6,416,970 B1
(45) Date of Patent: Jul. 9, 2002

(54) POTENTIALLY FLUOROGENIC COMPOUNDS

(75) Inventors: Günter Schabert, Goldach (CH); Lawrence Restaino, Chicago, IL (US)

(73) Assignee: Biosynth AG, Staad (CH)

( * ) Notice: Subject to any disclaimer, the term of this patent is extended or adjusted under 35 U.S.C. 154(b) by 0 days.

(21) Appl. No.: 09/646,528

(22) PCT Filed: Feb. 2, 1999

(86) PCT No.: PCT/EP99/00678
§ 371 (c)(1),
(2), (4) Date: Sep. 19, 2000

(87) PCT Pub. No.: WO99/48899
PCT Pub. Date: Sep. 30, 1999

(30) Foreign Application Priority Data

Mar. 23, 1998 (EP) ............................................. 98105195

(51) Int. Cl.[7] .............................. C12Q 1/04; C12Q 1/00

(52) U.S. Cl. ............................. 435/34; 435/4; 435/968; 435/975

(58) Field of Search ............................. 435/34, 4, 968, 435/975

(56) References Cited

U.S. PATENT DOCUMENTS

| | | | | |
|---|---|---|---|---|
| 3,772,340 A | | 11/1973 | Mhatre et al. ........... 260/343.2 |
| 5,364,767 A | | 11/1994 | Flowers et al. ................ 435/39 |
| 6,051,391 A | * | 4/2000 | Schabert et al. .............. 435/21 |
| 6,068,988 A | * | 5/2000 | Schabert et al. .............. 435/21 |

OTHER PUBLICATIONS

Witmer et al., U–3'–BCIP: a chromogenic substrate for the detection of RNase A in recombinant DNA expression systems, Nucleic Acids Research, vol. 19, No. 1, 1991, pp. 1–4.

Haikal, Synthesis of Guanosine–3'– (5–bromo–4–chloroinol–3–yl)–Phosphate (G–3'–BCIP), Collection of Czechoslovak Chemical Communications, vol. 61, No. 3, 1996, pp. 427–431.

Tsou et al., Synthesis of 5–Iodo–3–Indolylphosphodiesters of 5–Fluorodeoxyuridine as Possible Chromogenic Cancer Chemotherapeutic Agents, Journal of Medicinal Chemistry, vol. 13, No. 4, 1970, pp. 765–768.

Haugland, Handbook of Fluorescent Probes and Research Chemicals, 5th Ed. 1992–1994, Enzyme Substrates, pp. 81–88.

Hafner, et al., "Cyclohexyl Alkylphosphonofluoridates," *J. Med. Chem.*, vol. 13, No. 5, 1025–1027 (1970).

Shashidhar, et al., "A Fluorescent Substrate for the Continuous Assay of Phosphatidylinositol–Specific Phospholipase C: Synthesis and Application of 2–Naphthyl myo–Inositol–1–phosphate," *Anal. Biochem.*, 198:10–14 (1991).

(List continued on next page.)

*Primary Examiner*—Louise N. Leary
(74) *Attorney, Agent, or Firm*—Blank Rome Comisky & McCauley LLP (57) ABSTRACT

The invention provides compounds of formula (I) in which $R^1$, $R^2$, $R^3$, $R^4$ and $R^5$ are independently selected from hydrogen and chromogenic substituents, and X is selected from the group consisting of hydroxyl; $OR^6$ wherein $R^6$ is selected from the group consisting of $C_1$–$C_4$ alkyl; and $O^-Me^+$ wherein $Me^+$ is a cation derived from an organic or inorganic base. A preferred species of formula (I) is 4-Methylumbelliferyl myo-inositol-1-phosphate and salts thereof with an organic or inorganic base. The invention also provides fluorogenic methods for detecting various pathogenic bacteria, e.g., Listeria, Staphylococcus and Clostridium species, using substrates containing at least one formula (I) compound. A kit for detecting a phosphatidyl-inositol-specific phospholipase C enzyme as an indication of bacterial activity is disclosed.

18 Claims, 2 Drawing Sheets

OTHER PUBLICATIONS

Hendrickson, et al., "A Thiophosphate Substrate for a Continuous Spectophotometric Assay of Phosphatidylinositol-–Specific Phospholipase C: Hexadecylthiophosphoryl–1–myo–Inositol," *Bioorganic & Medical Chemistry Letters,* vol. 1, No. 11, pp. 615–618 (1991).

Shashidhar, et al., "Chromogenic Substrate for Phosphatidylinositol–specific Phospholipase C: 4–nitrophenyl myo–inositol–1–phosphate," *Chemistry and Physics of Lipids,* 60:101–110 (1991).

Yarborough et al., "Histochemistry of Macrophage Hydrolases III, Studies on beta–Galactosidase, beta–Glucoronidase and Aminopeptidase with Indolyl and naphthyl Substrates," J. Reticuloendothelial Soc. (1967) 4: 390–408.

Leigh, et al., "Substrate Stereospecificity of Phosphatidylinositol–Specific Phospholipase C from *Bacillus cereus* Examined Using the Resolved Enantiomers of Synthetic myo–Inostiol 1–(4–Nitrophenyl phosphate)", *Biochemistry* (1992).

Ryan, et al., "A Chemiluminescent Substrate for the Detection of Phosphatidylinositol–Specific Phospholipase C," *Analytical Biochemistry,* 214:548–556 (1993).

* cited by examiner

POTENTIALLY FLUOROGENIC COMPOUNDS

FIELD OF THE INVENTION

This is a National Phase Application of PCT/EP99/00678 filed Feb. 2, 1999, which in turn, claims priority of EP Application 98105195.6 filed Mar. 23, 1998.

The present invention relates to novel and potentially fluorogenic compounds which become fluorogenic and, hence fluoroscopically detectable upon contact with certain microorganisms or substances produced by such microorganisms, as well as to the use of such compounds for detection and identification of various bacteria.

PRIOR ART

Conventional assay procedures for identification of bacteria rely on traditional reactions, such as specific characteristics of acid production from particular carbohydrates, esculinase production, pH indicators, and generation of hydrogen sulfide. Such methods tend to be laborious and time consuming and, hence, are costly.

It is known that the enzyme termed "phosphatidylinositol-specific phospholipase C" i.e. 1-phosphatidyl-D-myo-inositol also known as inositolphosphohydrolase, also termed PI-PLC herein for short; enzyme classification EC 3.1.4.10 can be found in culture supernatants of various bacteria including *Bacillus thuringiensis* as well as some pathogenic bacteria such as *Listeria monocytogenes, Listeria ivanovii, Bacillus cereus, Staphylococcus aureus* and *Clostridium novyi* (cf. S. G. Rhee et al, Science 244 (1989) 546 ff).

More recently, Notermans et al. (Applied and Environmental Microbiology 57 (1991), 2666) have reported an assay method based upon analyzing for PI-PLC by overlaying *Listeria monocytogenes* colonies with a particular substrate, L-α-phosphatidyl-inositol, and examining for turbid halos around the colony indicating the presence of the enzyme. This method is a discontinuous one.

A prior art continuous assay for PI-PLC is based upon the use of 2-naphthyl myoinositol-1-phosphate as a substrate for fluorometric measurement of PI-PLC activity (c.f. M. S. Shashidhar, J. J. Volwerk, J. F. W. Keana, O. H. Griffith; Anal. Biochem. 198 (1991), 10). This substrate has two major disadvantages, however: while 2-naphthol has its maximum fluorescence intensity at pH 10.4, PI-PLC has an optimal pH at about pH 7.4 and is not active above pH 9.0.

OBJECTS AND SUMMARY OF THE INVENTION

Accordingly it is a primary object of the present invention to provide for novel and potentially fluorogenic compounds which avoid the disadvantages of prior art.

The term "potentially fluorogenic" as used herein with reference to the novel compounds according to the invention indicates the capacity of these compounds to become "fluorogenic"—i.e. fluoroscopically active and detectable by fluoroscopic methods—upon interaction with PI-PLC.

Further objects of the invention include improved means for detecting and identifying various pathological bacterias, such as Listeria sp.

The above and further objects and advantages as apparent from the specification will be achieved according to a first embodiment of the invention by potentially fluorogenic compounds of formula (I)

in which $R^1, R^2, R^3, R^4$ and $R^5$ are independently selected from the group consisting of hydrogen and chromogenic substituents, while X is selected from the group consisting of hydroxyl; $OR^6$ wherein $R^7$ is selected from the group consisting of $C_1$–$C_4$ alkyl; and $O$-$Me^+$ wherein $Me^+$ is a cation derived from an organic or inorganic base.

While no theoretical limitation is intended, the effectiveness of compounds of formula (I) as substrates for PI-PLC detection is believed to reside in the fact that cleavage of a compound according to the invention by bacterial PI-PLC results mainly in the formation of inositol 1,2-cyclic phosphate and 4-methylumbelliferone which is fluorogenic.

According to a second embodiment, the invention provides for a method of detecting microbial activity in a sample, e.g. in the manner of a screening test, by combining the sample with a compound of formula (I) or a salt thereof and inspecting the sample combined with the formula (I) compound or the salt thereof, preferably as its resulting mixture, by fluoroscopic means.

According to a third embodiment, the invention provides for a method of identifying a bacterial microorganism of interest which is capable of producing a phosphatidyl-inositol-specific phospholipase C enzyme by:

(A) providing a test sample suspected of containing the microorganism of interest;

(B) submitting the test sample to a pre-enrichment step;

(C) combining a portion, at least, of the product obtained in step (B) with a compound of formula (I) to provide a screening sample which exhibits a positive fluoroscopic response when the microorganism of interest or the PI-PLC it produced is present in the test sample;

(D) if the screening sample shows a positive fluoroscopic response in step (B) a portion, at least, of the product obtained in step (B) is transferred to a medium suitable for culturing the microorganism; the medium contains at least one compound capable of producing a colour when exposed to the microorganism;

(E) cultivating the medium with the transferred portion for developing at least one colony exhibiting color; and (F) recovering a portion, at least, of the coloured colony for final identification.

According to a third embodiment, the invention provides for a substrate for detecting PI-PLC as an indication of bacterial activity; the substrate contains at least one compound of formula (I) in a suitable medium, such as aqueous agar-agar.

According to a fourth object, the invention provides for a kit for detecting PI-PLC as an indication of bacterial activity; the kit includes at least one compound of formula (I).

According to yet a further object, the invention provides for a method of producing a compound of Formula (I) by converting a compound of formula (IIIA) into the compound of formula (IIIB) according to the reaction (IIIA)

(IIIB)

in which "Ins" represents inositol and G represents a HO-protecting group on each hydroxyl of the inositol except the 1-hydroxy, and wherein X and $R^1$–$R^5$ have the meaning indicated above for formula (I); removing the HO-protecting groups; and optionally forming a salt by reaction with an organic or inorganic base when X represents hydroxyl.

PREFERRED EMBODIMENTS OF THE INVENTION

Compounds of formula (I) and (II)—also termed "substrates" herein in view of their interaction with an enzyme—may be obtained and used in racemic form and such mixtures can be resolved to obtain the enantiomers. It is to be expected, however, that no substantial advantages will normally be obtained with the enantiomers.

Accordingly, use of racemic mixtures of formula (I) and (II) compounds will be a preferred form of the invention.

Examples of suitable organic and inorganic bases preferred for use according to the invention in its various embodiments including but not restricted to formula (I) when X is hydroxy, or $O^-Me^+$, respectively, are sodium hydroxide, potassium hydroxide, lithium hydroxide, ammonium hydroxide, diethylamine, triethylamine, tetramethylammonium hydroxide, tetraethylammonium hydroxide, cyclohexylamine, pyridine, piperidine, pyrrolidine, morpholine, N-methyl-morpholine, N-ethyl-morpholine and p-toluidine.

A preferred group of compounds of formula (I) are those wherein the chromogenic substituents are: $C_1$–$C_4$ alkyl groups, i.e. methyl, ethyl, propyl and butyl including the isomeric forms, optionally containing an oxygen atom in the alkyl chain; $C_1$–$C_4$ alkoxy; nitro; carboxy, $C_1$–$C_4$ carboxyalkyl; and cyano; optionally, the alkyl groups just mentioned may include one or more halogen atoms, preferably fluorine, chlorine and bromine, as substituents; the trifluoromethyl group is a specific example of a preferred halo-substituted alkyl for use as chromogenic substituent in formula (I).

An even more preferred group of formula (I) compounds includes those wherein $R^3$ is a lower alkyl optionally containing one or more halogen atoms, X is hydroxyl, and $R^1,R^2,R^4$ and $R^5$ are hydrogen while $R^3$ is a lower alkyl or alkoxy group.

A preferred specific novel compound of formula (I) is 4-methyl umbelliferyl myo-inositol-1-phosphate and the salts thereof with organic or inorganic bases of the type set forth above this compound has the formula:

(II)

A most preferred compound for use as a fluorogenic substrate according to the invention is the N-methyl-morpholine salt of 4-methylumbelliferyl myo-inositol-1-phosphate. It will be referred to as "MeU-phos-inositol" herein for brevity. It is a colorless and water-soluble substance having its UV-maximum (in Tris/HCl-buffer at a pH-range of 7 to 9) at 314 nm with an absorption coefficient of ≈10800 1 $mol^{-1}$ $cm^{-1}$.

Upon contact with PI-PLC, a potentially fluorogenic compound of formula (I) and (II), respectively, according to the invention becomes a strong fluorophore which can be easily detected, e.g. by a conventional hand held fluorometer, e.g. for operation at a wavelength in the ultra-violet range which is favorable for practical purposes, such as 366 nm. This simple detection approach can be used, according to the invention, either as a screening test and/or as a first step in a more elaborate identification test. In the screening test, lack of fluorescence can be considered a "negative" reaction in the sense that no further testing is required and only a "positive" reaction of the primary samples needs to be verified by additional testing.

More specifically, 4-methylumbelliferone (resulting from cleavage of the formula (II) by PI-PLC has an absorption maximum of 360 nm at pH values above 8 whereas the corresponding formula (I) compounds show only a negligible absorption at 360 nm.

In other words, 4-methylumbelliferone (4-methyl-7-hydroxycoumarin) is a very good fluorogen. Generally, the intensity of fluorescence of 4-methylumbelliferyl substrates is the same at pH 7 and pH 10 whereas the fluorescence of the product of cleavage increases at pH values in this range. Generally, the enzymatically cleaved substance is preferably determined fluorometrically at a pH near 9.5.

At pH 9.5 typical substrates using 4-Methylumbelliferone as fluorophor show fluorescence emission with maxima around 380 nm (excitation maxima at 325 nm) whereas 4-methylumbelliferone has its fluorescence maximum at 448 nm (excitation maximum 364 nm)

Turning to detection methods according to the invention, the term "primary sample" used herein refers to the material obtained directly from a suspected source that may be of physiological or other origin, such as blood, excrement, or infected foods, water sources, drinks or the like materials capable of harbouring the bacteria of interest. The invention is of particular use for detecting and isolating Listeria, Staphylococcus and Clostridium. An important application of the invention is detection of such human pathogens, as *Listeria monocytogenes*.

When using a compound of formula (I) or (II) in a screening or identification test for bacterial activity as evidenced by the presence of PI-PLC, it may be advantageous to provide a pre-enrichment broth in which the primary sample is transferred in order to increase the bacterial activity prior to fluoroscopic analysis. It is preferred for many applications of the inventive method to use a pre-enrichment broth which, in addition, may be selective for the bacteria of interest. The term "pre-enrichment broth" which may be but need not be selective is understood by those experienced in the art who are capable of selecting a pre-enrichment broth that is most suitable for the bacteria of interest. Generally, inhibition of growth of other bacteria producing PI-PLC enzyme can be accomplished using various combinations of selective compounds including antibiotics and other inhibitors and the medium can be made specific for any pathogen that contains or produces PI-PLC. More specific examples will be given below.

In both of its aspects as a screening and identification test, respectively, the invention provides for means to indicate bacterial activity of microorganisms having PI-PLC activity, including the nonpathogenic *Bacillus thuringiensis* as well as the pathogenic *Bacillus cereus, Listeria monocytogenes, Listeria ivanovii, Staphylococcus aureus, Clostridium novyi, Trypanosoma brucei*.

As indicated above, a more complete identification step includes the use of a formula (I) compound as a potential fluorogenic agent as well as interaction with a potential chromogenic agent. A colour will be formed in the presence of such a chromogenic agent if bacterial PI-PLC is produced by the bacteria of interest in the culture medium and will localise the colony.

A group of preferred chromogenic agents for producing a colour when exposed to PI-PLC has been disclosed in our and U.S. Pat. Nos. 6,051,391 and 6,068,988, which issued on Apr. 18, 2000 and May 30, 2000, respectively, each based on Provisional Application Serial No. 60/039,479, copending U.S. patent application Ser. No. 60/039 479 and in our international application WO 98/38332, respectively. Generally, such agents have the formula wherein $R^{11}$ is hydrogen or a $C_1$–$C_4$ alkyl and $R^6$, $R^7$, $R^8$, $R^9$ and $R^9$ are selected from hydrogen and chromogenic substituents while $R^{10}$ is hydrogen or $C_1$–$C_4$ alkyl; again, as in the case of formula (I) compounds, salts of formula (IV) compounds with an organic or inorganic base of the type mentioned above can be used as according to the invention.

In a group of preferred compounds of formula (IV), $R^6$ and $R^9$ are halogen atoms, preferably chlorine and bromine, while $R^8$, $R^9$, $R^{10}$ are hydrogen; again, the salts of formula (IV) compounds with organic or inorganic bases of the type exemplified above can be used as the potential chromophore, i.e. yielding deeply coloured indigo dyes upon cleavage by PI-PLC, dimerization and subsequent oxidation, especially wherein $R^{10}$ is hydrogen or methyl and the other substituents hydrogen, fluoro, chloro, bromo, iodo, cyano, nitro, carboxy, substituted or unsubstituted amino, substituted or unsubstituted aminomethyl or sulfonyl.

A most preferred compound of formula (IV) for use as chromogenic substrate according to the present invention are the salts of 5-bromo-4-chloro-3-indoxyl myo-inositol-1-phosphate. The ammonium salt of this compound is termed "X-phos-inositol" herein below for brevity.

A preferred test method for identifying *Listeria monocytogenes* will now be explained in more detail and comprises use of a pre-enrichment broth that can repair or resuscitate injured *Listeria monocytogenes* cells. After the cells have repaired, the broth can support a rapid growth of *Listeria monocytogenes* cells. This medium contains inhibitor(s) which will not prevent the repair of injured *Listeria monocytogenes* cells but can prevent the growth of some Gram negative bacteria that could outcompete *Listeria monocytogenes* cells for nutrients in the broth.

Then, a selective enrichment broth, that contains the fluorogenic substrate, preferably a 4-methylumbelliferyl myo-inositol-1-phosphate of formula (II) as defined above, is inoculated with a portion, at least, of the pre-enrichment broth. This selective enrichment broth contains inhibitors that prevent growth of other bacteria containing PI-PLC enzyme (other than *Listeria ivanovii*) and Gram positive bacteria closely related to *Listeria monocytogenes*.

Subsequent to incubation, the selective enrichment broth is exposed to a UV fluorometer (long wavelength at 366 nm) and examined for fluorescence. A positive fluorogenic reaction indicates a presumptive positive test requiring further testing and no fluorescence means no *Listeria monocytogenes* is present in the sample tested (no further testing needed).

After incubation of the selective enrichment and the occurrence of fluorescence, a small portion, e.g. a wire loop transporting a small amount of liquid, is streaked on the selective plating medium containing a potentially chromogenic compound of formula (IV). If *Listeria monocytogenes* is present, the cells will grow on the plating medium producing a colony which will show the colour developed by of the chromogenic compound when in contact with PI-PLC. Preferably, this plating medium is made selective as well to prevent growth of other bacteria, except *Listeria ivanovii*, containing the PI-PLC enzyme and Listeria related Gram positive bacteria giving *Listeria monocytogenes* an optimal environment to produce an isolated colony.

Verification of the chromogenic colony (e.g. for a substrate containing 5-bromo-4-chloro-3-indoxyl myo-inositol-1-phosphat of formula (IV)) *Listeria monocytogenes* colony color is turquoise to blue). The colony can be isolated for further testing if required.

The chromogenic substrate works best on a solid surface since the color of the chromogen will be retained within the cell causing the color of the colony to be the color of the chromogen. The chromogen is water insoluble which allows for the color to remain in the colony. Therefore, the chromogenic substrate would not be efficacious in a broth since the color of the chromogen will not cause the color of the broth to change.

Plating media containing X-phos-inositol as chromogenic substrate tend to have very good stability. After 12 weeks of storage at 4° C., color and selectivity of the plating medium is the same as that of the freshly prepared medium. The *Listeria monocytogenes* colonies appear turquoise to blue and convexed, 1.0–2.5 mm in diameter without or with a turquoise to blue halo.

Compounds of formula (I) or their salts can be obtained according to the above reaction scheme by treating, in a first process step, 4-methylumbelliferyl-dichlorophosphate (IIIA) with a reactive inositol compound, e.g. a OH-protected inositol having a free hydroxyl group in 1-position (termed "G-Ins-OH" below) so as to obtain an intermediate product, e.g. by stirring the reactants in an organic base, such as pyridine, N-methyl-morpholine or triethylamine, as a reaction medium at ambient temperature during a period of several hours (e.g. 1–10 hours).

G is the protecting group on each hydroxyl of inositol except the 1-hydroxy; typical examples for G include optionally substituted benzyl, optionally substituted $C_{3-6}$ alkylidene (e.g. isopropylidene, cyclopentylidene or cyclohexylidene); and optionally substituted tetrahydropyranyl.

In the subsequent reaction step, all protecting groups G on the intermediate are removed, e.g. by hydrogenolysis or acidic cleavage depending upon the nature of the OH-protecting groups. Finally, the preferred salt can be obtained by ion exchange.

It will be apparent that such a synthesis method is capable of producing the novel formula (I) compounds efficiently in sufficiently large quantities as are required for application in standard screening procedures.

Based upon storage tests made with the lithium salt and the N-methyl-morpholine salt of 4-Methylumbelliferyl myoinositol-1-phosphate it is to be expected that the novel substrates (I) according to the invention are stable for extended periods of time when stored in a solid state at temperatures below about −15° C. and protected from light. Fluorogenic substrates of formula (I) show good stability in a selective enrichment broth medium. When stored in a typical selective enrichment broth at 4° C. in the dark, the shelf life of the fluorogenic substrate was 4 weeks.

On the other hand, compounds of formula (I) proved to be only moderately stable at room temperature in conventional buffer solutions (sodium citrate, Tris/HCl) for several hours at pH values ranging from 5 to 7 and are not stable at alkaline pH values. The rate of decomposition increases with the pH. At a pH value of 8.5 the rate of cleavage by PI-PLC is similar to the rate of decomposition (rates≈0.35 $\mu$Mol $l^{-1}$ $min^{-1}$ in 1 mM solutions). At pH 9 decomposition proceeds rapidly and at pH values above 10 decomposition is extremely fast.

As a consequence, continuous spectrophotometric monitoring of the cleavage of formula (I) substrates by PI-PLC is not preferred.

On the other hand, a calorimetric assay of PI-PLC using the novel substrates of formula (I) can be conducted effectively at pH values in the range from 6 to 7 where self decomposition in buffer solutions is very slow. Furthermore the enzyme works best at a pH value around 7 and the activity does not vary much between pH 5 and 8.5.

As the absorbance of 4-methylumbelliferone at 360 nm is negligible at a pH of 6, the enzymatically liberated 4-methylumbelliferone is best detected in a discontinuous manner.

Accordingly, enzymic cleavage of the new substrates of formula (I) preferably is conducted at a pH around 6 or 7 and the amount of liberated 4-methylumbelliferone is determined after defined periods of time by raising the pH of a sample to about 9.5, e.g. by addition of a sufficient amount of 1 N sodium hydroxide solution and immediate measurement of the absorbance of the anion of 4-methylumbelliferone with a spectrophotometer.

According to this embodiment of the invention, the novel substrates of formula (I), preferably the N-methylmorpholine salt, are used for a sensitive calorimetric assay of PI-PLC from *Bacillus cereus*; to this end, the substrate is used in combination with serum albumin, e.g. bovine serum albumin (BSA).

Compared with the prior art substrate 2-NIP mentioned above, MeU-phos-inositol in combination with BSA shows high turnover rates when cleaved by PI-PLC.

It is expected that the novel substrates of formula (I) can be used for a continuous fluorometric assay of PI-PLC: While the intensity of fluorescence of 4-methylumbelliferone has its maximum at pH values above 10, fluorescence intensity is sufficiently high at a pH of 6 or 7 to be utilized for a sensitive assay of PI-PLC.

As a consequence, the fluorogenic substrate (I) tends to be more efficacious in a broth medium than on a solid medium, such as agar, where the fluorescence may leach from the colony into the agar medium causing other nearby colonies to be misread.

Consequently, a positive reaction (secretion of the PI-PLC enzyme by a bacterial species in a broth medium) in the presence of the fluorogenic substrate will cause the broth to show fluorescence indicating that a PI-PLC secreting bacterial species is in the broth at a significant cell density.

This is a presumptive positive reaction for the bacterial species of interest (such as *Listeria monocytogenes*) which warrant further isolation of the bacterial species in the form of a colony on a solid agar surface using the chromogenic substrate (IV) of the PI-PLC enzyme as explained above.

Use of both a fluorogenic substrates of formula (I) and a chromogenic substrate of formula (IV) in an overall isolation procedure allows for a presumptive positive reaction in the broth (the use of the fluorogenic substrate) followed by isolating the colony on a solid medium using the chromogenic substrate as more of a confirmatory reaction.

BRIEF DESCRIPTION OF DRAWINGS

The invention will now be explained in more detail by way of examples and with reference to the enclosed drawings in which.

It is to be noted, however, that the specific examples are not intended to limit the invention in any way.

EXAMPLES

Preparation of the New Substrates

Example 1

Preparation of the Lithium and N-methylmorpholine Salt of 4-Methylumbelliferyl Myo-inositol-1-phosphate 2,3:5,6-Di-isopropylidene-4-(4-methoxy-tetrahydropyran-4-yl-)-myo-inositol (cf. M. S. Shashidar et al., Chem. Phys. Lipids 60 (1991), 101) was prepared as described in this reference.

Crude 4-methylumbelliferyl-dichlorophosphate (containing approximately one equivalent of pyridine hydrochloride) was prepared by the method described for 1-acetyl-5-bromo-4-chloro-indoxyl-3-dichlorophosphate by J. P. Horwitz et al. in J. Med. Chem. 13 (1970), 1024.

Step 1: Preparation of the Pyridine Salt of 4-methylumbelliferyl[2,3:5,6-di-isopropylidene-4-(4-methoxytetrahydropyran-4-yl)-myo-inositol]-1-phosphate Crude 4-methylumbelliferyl-dichlorophosphate (1.80 g, corresponding to 1.28 g, 4.37 mMol, pure substance) was suspended under nitrogen in dry pyridine (13 ml) and 2,3:5,6-Di-isopropylidene-4-(4-methoxy-tetrahydropyran- 4-yl-)-myo-inositol (0.93 g, 2.48 mMol) was added after 20 minutes. The mixture was well stirred overnight.

The grey-brown solution containing some solid matter was cooled in an ice bath: then, water (4 ml) was added whereby the temperature rose to 16° C. and the solid dissolved rapidly. After removing the ice bath, chloroform (25 ml) was added. The solution was then stirred for an additional period of ten minutes. The organic phase was separated and the aqueous phase was extracted with chloroform (10 ml) and then discarded.

The combined organic phases were extracted twice with water and the combined aqueous extracts re-extracted three times with chloroform (10 ml). The combined organic phases and extracts were dried over anhydrous sodium sulphate and evaporated in vacuo. The slightly yellow solid obtained was dissolved in chloroform (10 ml) and re-evaporated in vacuo leaving a beige crystalline solid which was further dried in vacuo (1.45 g, yield 84%). $C_{33}H_{42}NO_{13}P$ (MW=691.67)

400 MHz $^1$H-NMR ($D_2O$): δ 1.14 (s, 3H), 1.34 (s, 3H), 1.36 (s, 3H), 1.47 (s, 3H), 1.70–1.95 (m, 4H), 2.39 (d, 3H), 3.28 (s, 3H), 3.63 (m, 2H), 3.74 (m, 2H), 3.97–4.08 (m, 4H), 4.68 (t, 1H), 4.83 (m, 1H), 6.16 (d, 1H), 7.32 (dd, 1H), 7.41 (d, 1H), 7.48 (d, 1H), 7.75 (t, 2H), 8.24 (t, 1H), 8.83 (d, 2H).

Step 2: Preparation of the Crude Pyridine Salt of 4-Methylumbelliferyl Myo-inositol-1-phosphate 4-Methylumbelliferyl [2,3:5,6-di-isopropylidene-4-(4-methoxy-tetrahydropyran-4-yl)-myo-inositol]-phosphate in the form of the pyridine salt (1.04 g, 1.5 mMol) was suspended in acetic acid/water 1:1 (10 ml) and stirred at 50° C. for three hours. The almost clear solution was evaporated in vacuo; the pale yellow oil obtained was dissolved in water (8 ml) and extracted four times with ethyl acetate (10 ml) and the pale yellow aqueous solution filtered and co-evaporated with ethanol (10 ml). Ethanol was added to the yellow, clear oil (10 ml); the resulting solution was evaporated again to obtain the crude pyridine salt as a light-yellow resin (0.68 g, yield 91%). $C_{21}H_{24}NO_{11}P$ (MW=497.39)

Step 3a: Preparation of the Lithium Salt of 4-Methylumbelliferyl Myo-inositol-1-phosphate Dowex® 50×8 cation-exchange resin (2.2 g) was suspended in water (1.6 ml) and a solution of the above crude pyridine salt of 4-Methylumbelliferyl myo-inositol-1-phosphate (0.75 g) in water (4.5 ml) was added. The suspension was stirred for five minutes and the resin was then removed by filtration.

To the pale yellow filtrate obtained, a solution of lithium hydroxide monohydrate (0.05 g in 1 ml of water) was added dropwise until a pH of 6 was reached (approximately 0.72 ml were needed).

The solution was extracted three times with ethyl acetate (6 ml) and the aqueous phase evaporated in vacuo. The yellow oil obtained was taken up in methanol (3 ml) and added dropwise to well stirred acetone (60 ml). The fine precipitate was stirred for a further hour, then left in the refrigerator overnight. The white solid was collected by filtration, washed with acetone and dried in vacuo (0.58 g, yield 91%).

Anal. Calcd for $C_{16}H_{18}O_{11}PLi$ (MW=424.22): C 45.30, H 4.28, P 7.30, Li 1.64; Found (on dry matter): C 44.51, H 4.39, P 7.3, Li 1.66, (water content 7.7%).

400 MHz $^1$H-NMR ($D_2O$) δ 8 2.30 (d, 3H), 3.17 (t, 1H), 3.39 (dd, 1H), 3.49 (t, 1H), 3.63 (t, 1H), 3.95 (m, 1H), 4.11 (t, 1H), 6.13 (d, 1H), 7.10 (m, 2H), 7.60 (d, 1H). UV (4 mg in 100 ml buffer Tris-HCl, pH 7): $\lambda_{max}$=314 nm; ε=10100 mol$^{-1}$ cm$^{-1}$.

Step 3b: Preparation of the N-Methyl-morpholine Salt of 4-Methylumbelliferyl Myo-inositol-1-phosphate (MeU-phosinositol)

Dowex 50W×8 cation-exchange resin (2.2 g) was suspended in water (1.6 ml) and a solution of the above crude pyridine salt of 4-Methylumbelliferyl myo-inositol-1-phosphate (0.75 g) in water (4.5 ml) was added. The suspension was stirred for five minutes and the resin was then removed by filtration.

To the pale yellow filtrate N-methyl-morpholine (approximately 0.18 ml) was added dropwise until a pH of 6 was reached. The solution was extracted three times with ethyl acetate (6 ml) and the aqueous phase was evaporated in vacuo. The yellow oil obtained was taken up in methanol (3 ml) and added dropwise to well stirred acetone (60 ml). The precipitate was stirred for a further hour, then left in the refrigerator overnight. The white solid was collected by filtration, washed with acetone and dried in vacuo (0.74 g, yield 95%).

Anal. Calcd for $C_{21}H_{30}NO_{12}P$ (MW=519.44): C 48.56, H 5.82, N 2.70, P 5.96; Found (dry: C 48.25, H 5.93, N 2.66, P 5.90, (water content 4.1%).

400 MHz $^1$H-NMR ($D_2O$) δ 2.32 (d, 3H), 2.75 (s, 3H), 3.03 (m, 2H), 3.17 (t, 1H), 3.30 (m, 2H), 3.39 (dd, 1H), 3.49 (t, 1H), 3.62 (m, 2H), 3.63 (t, 1H), 3.93 (m, 2H), 3.95 (m, 1H), 4.11 (t, 1H), 6.15 (d, 1H), 7.11 (m, 2H), 7.62 (d, 1H). UV (4 mg in 100 ml buffer Tris-HCl of pH 7): $\lambda_{max}$=314 nm; ε=10900 mol$^{-1}$ cm$^{-1}$.

Example 2

Stability of the Fluorogenic Substrate in Buffer Solutions at Different pH Values In this example, a Perkin-Elmer Lambda 15 Spectrophotometer was used for the experiments which were conducted at ambient temperature (about 25° C.).

The stability of the new fluorogenic substrate MeU-phos inositol was investigated in 3 ml cuvettes in buffer solutions containing 0.1% bovine serum albumin (BSA) under various pH conditions (0.1 M sodium citrate buffers of pH 5 and 6; 0.1 M Tris/HCl buffers of pH 7, 8 and 8.5) followed by spectrophotometric detection of 4-methyl-umbelliferone at 360 nm either by continuous measurement or (for pH values <8) by discontinuous measurement (rising the pH to 9.5) as described in example 3 below.

The results (c.f. Table 1) show that the fluorogen was liberated under the conditions of enzyme assay when the pH was alkaline. This non-enzymatic hydrolysis was linear if plotted versus time and substrate concentration, and rose markedly with rising pH values.

TABLE 1

Rates of hydrolysis of MeU-phos-inositol

| Substrate concentration (nM) | pH | Enzyme | Rate [nMol l$^{-1}$min$^{-1}$] |
|---|---|---|---|
| 1 | 8.5 | – | 330 |
| 5 | 8.5 | – | 1780 |
| 5 | 8 | – | 470 |
| 5 | 7 | – | <5 |
| 5 | 6 | – | stable |
| 5 | 5 | – | stable |
| 1 | 8.5 | + | 720 |
| 5 | 8.5 | + | 2140 |

These results confirm that the rates increase upon addition of enzyme solution (2 μl, cf. example 3) indicating an enzymatic cleavage of the substrate by PI-PLC at pH 8.5.

As the rates of hydrolysis are comparable to or even higher than the rates of enzymic cleavage, an assay of PI-PLC does not yield meaningful results if conducted at an alkaline pH.

Example 3

Colorimetric Assay of PI-PLC Using MeU-phos-inositol

In this example, a Perkin-Elmer Lambda 15 Spectrophotometer was used for the experiments which were conducted at ambient temperature (about 25° C.).

The procedure for the detection of PI-PLC was as follows:

MeU-phos-inositol was dissolved in 25 ml of 0.1 M sodium citrate buffer of pH 6.0 containing 0.1% of bovine serum albumin (BSA).

An aliquot from a stock solution of PI-PLC (Boehringer Mannheim #1143 069; specific activity 600 U/mg corresponding to 10.002 kat/kg, 5U/100 µl solution, corresponding to 8.33 µg/100 µl) was added.

After defined periods of time 3 ml of the solution were transferred to a cuvette.

The enzymatically liberated 4-methylumbelliferone was converted into the anionic form by addition of 0.05 ml of 1 N sodium hydroxide solution (pH rose to approximately 9.5). The photometer readings at 360 nm were noted immediately for different enzyme concentrations.

Figure 1:
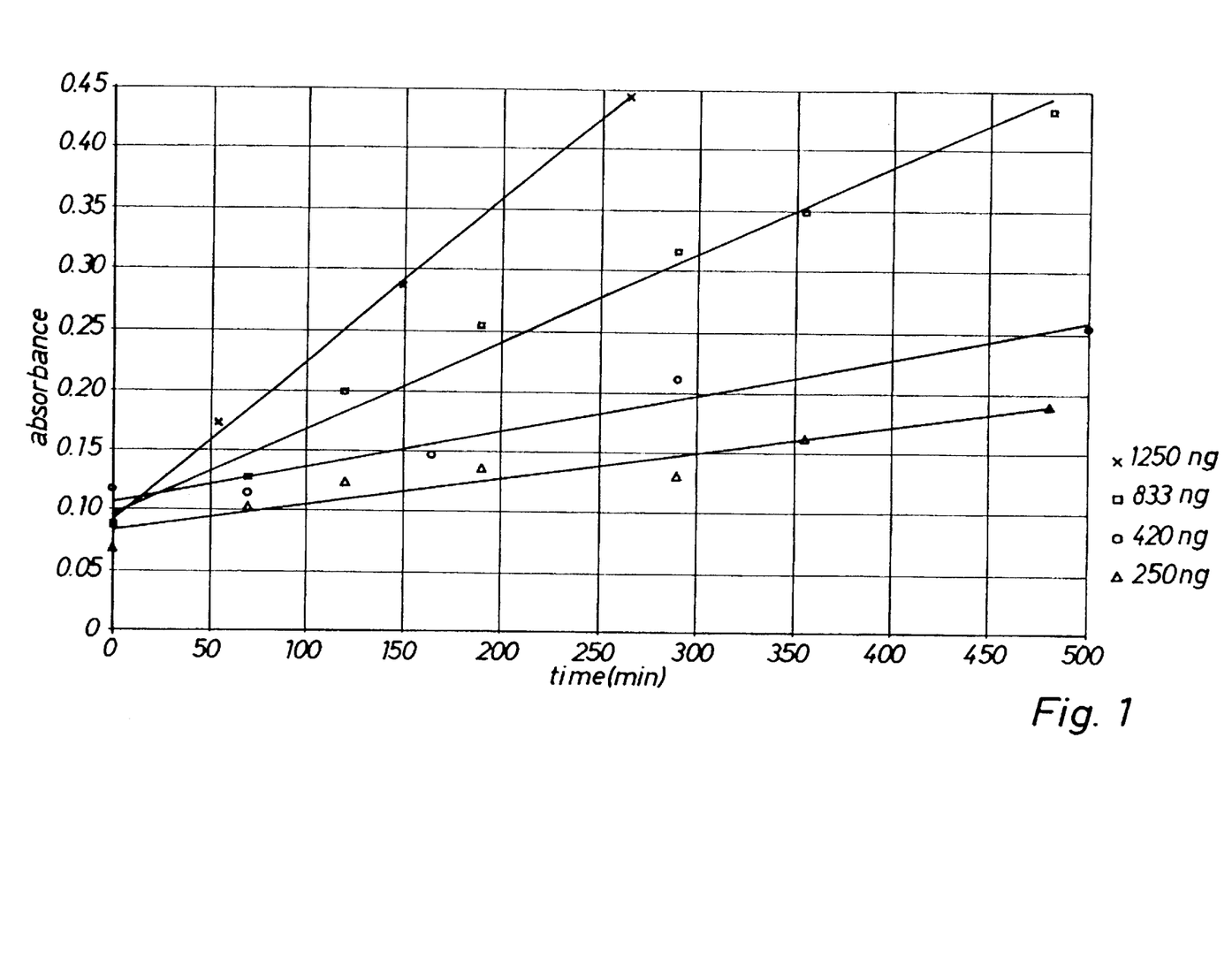
FIG. 1 is a graph showing dependence of the absorbance (on the ordinate) upon time (on the abscissa) at various enzyme concentrations in a buffer solution of pH 6.0 obtained by discontinuous measurement at a substrate concentration of 1 mM.

FIG. 1 shows the absorbance as a function of time for different enzyme concentrations at a substrate concentration of 1 mM. The cleavage rates [nMol $l^{-1}min^{-1}$] and the specific enzyme activities are shown in Table 2.

TABLE 2

Dependence of rate of cleavage and specific activity on enzyme concentration at pH 6.0

| Amount of enzyme [µl stock solution] | [ng] | Rate [nMol $l^{-1}min^{-1}$] | Specific Activity [µMol $min^{-1}mg^{-1}$] |
|---|---|---|---|
| 3 | 250 | 13.2 | 1.32 |
| 5 | 417 | 18.2 | 1.08 |
| 10 | 833 | 43.4 | 1.30 |
| 15 | 1250 | 80.2 | 1.60 |

The specific activity of the new substrate (at pH 6) is at least 30 fold higher as was the case with the prior art substrate 2-NIP mentioned above. As the turnover rate of PI-PLC has its maximum around pH 7, the specific activity will further increase when the assay is conducted at a pH of 7.

At pH 6 the limit of detection or sensitivity at a substrate concentration of 1 mM is below 100 ng of enzyme.

The limit of detection will be even lower when the assay is conducted at pH 7. Additionally the substrate concentration may be increased.

Figure 2:
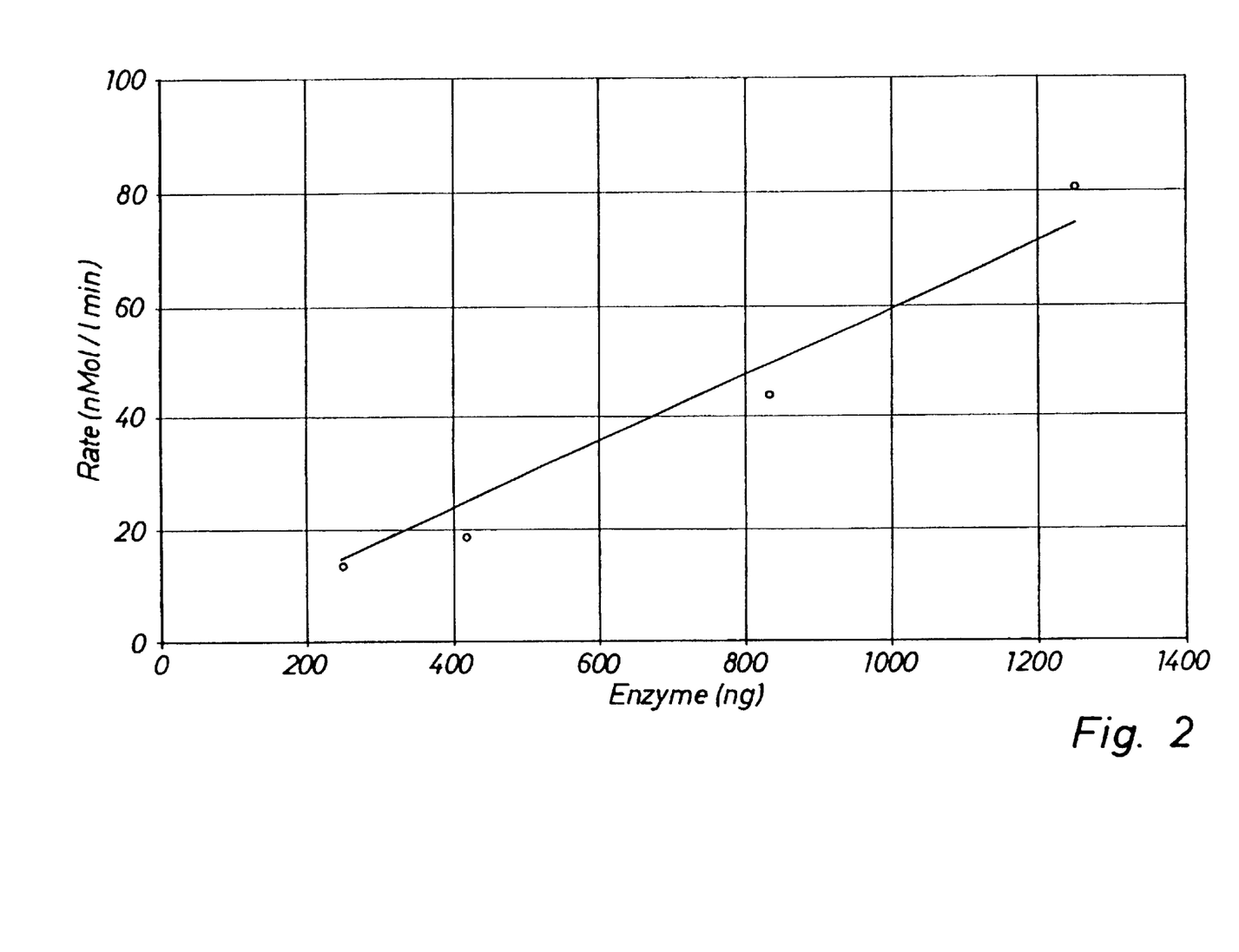
FIG. 2 is a graph showing the rate of substrate cleavage (ordinate, in nMol $l^{-1}$ $min^{-1}$) as a function of the amount of enzyme (abscissa, in nanogramms).

A plot of the rates versus amount of enzyme added (cf. FIG. 2) indicated satisfactory linearity.

Example 4

Pre-enrichment Broth for the Isolation of *Listeria monocytogenes*

This example includes inoculation, preparation and efficacy of the pre-enrichment broth. The pre-enrichment medium consisted of the following:

| | |
|---|---|
| Proteose Peptone (ex Difco) | 5.0 grams/liter |
| Glucose | 3.0 grams/liter |
| Tryptone (ex Difco) | 5.0 grams/liter |
| Yeast Extract (ex Difco) | 6.0 grams/liter |
| Beef Extract, desiccated (ex Difco) | 5.0 grams/liter |
| Sodium Phosphate (dibasic) | 9.6 grams/liter |
| Potassium Phosphate (monobasic) | 1.35 grams/liter |
| Sodium Pyruvate | 10.0 grams/liter |
| Nalidixic acid (ex Sigma) | 0.03 grams/liter |

All components were dissolved in 1 liter of water (deionized or distilled). A cap was placed on top of the container and the contents of the flask were autoclaved for 15 minutes at 121° C.

The broth was cooled to room temperature. The stability of the broth was 12 weeks held at room temperature either in the light or dark. For detection of *Listeria monocytogenes*, the specimen were rehydrated with the pre-enrichment broth at a ratio of 1:10 and thoroughly mixed. The inoculated pre-enrichment broth was incubated at 30° C. for 22–24 hours.

The broth is selective by not allowing the growth of various Gram negative bacteria (these bacteria could outgrow *Listeria monocytogenes* in the broth) and some Gram positive bacteria (shown in Table 3) without preventing the repair of injured and subsequent growth of *Listeria monocytogenes* cells (cf. Table 4).

TABLE 3

Inhibition of various bacterial strains in the pre-enrichment broth containing 30 mg/liter of nalidixic acid

| | Colony forming units/ml | |
|---|---|---|
| Bacterial strain | at start | after 24 hours/30° C. |
| Salmonella enteritidis | 115,000 | 25 |
| Pseudomonas aeruginosa ATCC 15442 | 88,000 | 1,260,000,000 |
| Kiehsiella pneumoniae | 105,000 | 35 |
| Yersinia enterocolitica ATCC 27729 | 41,000 | <10 |
| Escherichia coli ATCC 25922 | 140,000 | 170 |
| Providencia stuartii | 130,000 | 420 |
| Hafnia alvei | 191,000 | 150 |
| Acinetobacter calcoaceticus | 62,000 | 15 |
| Enterobacter aggiomerans | 211,000 | 60 |
| Citrobacter freundii | 95,00C | 140 |
| Escherichia coli ATCC 8739 | 49,0CC | 15 |
| Escherichia coli O157:H7 ATCC 35150 | 131,000 | <10 |
| Staphylococcus aureus ATCC 6538 | 81,000 | 52,000 |
| Staphylococcus epidermidis | 91,000 | 90,000,000 |
| Bacillus cereus | 91,000 | <10 |
| Bacillus thuringiensis | 7,500 | <10 |
| Enterococcus faecium ATCC 19434 | 121,000 | 710,000,000 |
| Enterococcus feacalis | 142,000 | 450,000,000 |
| Pediococcus cerevisiae | 149,000 | 480,000,000 |
| Pseudomonas fluorescens ATCC 13525 | 47,000 | 4,200 |
| Listeria monocytogenes 4b | 105,o00 | 2,440,000,000 |
| Listeria monocytogenes 3b | 119,000 | 2,490,000,000 |
| Listeria monocytogenes ATCC 43249 | 196,000 | 2,300,000,000 |
| Listeria monocytogenes ATCC 19114 | 146,000 | 2,910,000,000 |
| Listeria monocytogenes ATCC 19116 | 94,000 | 2,000,000,000 |

TABLE 3-continued

Inhibition of various bacterial strains in the pre-enrichment broth containing 30 mg/liter of nalidixic acid

| | Colony forming units/ml | |
|---|---|---|
| Bacterial strain | at start | after 24 hours/30° C. |
| Listeria monocytogenes ATCC 19117 | 172,000 | 2,670,000,000 |
| Listeria monocytogenes Scott A | 181,000 | 3,150,000,000 |
| Listeria monocytogenes ATCC 35152 | 116,000 | 560,000,000 |
| Listeria ivanovii | 72,000 | 3,130,000,000 |
| Listeria welshimeri | 88,000 | 2,14C,000,000 |
| Listeria seeligeri | 118,000 | 3,740,000,000 |
| Listeria grayi | 34,000 | 2,180,000,000 |
| Listeria innocua | 159,000 | 3,190,000,000 |

TABLE 4

Recovery of injured Listeria monocytogenes cells in the ore-enrichment broth

| Listeria monocytogenes strain/media | Time in hours broth stored at 30° C. )$^a$ | | | | |
|---|---|---|---|---|---|
| | 0 h | 3 h | 5 h | 7.5 h | 10 h |
| L. monocytogenes ATCC 19114 nonselective nutrient broth | 2.34 )$^b$ | 1.57 | 1.15 | 0.79 | 0.09 |
| pre-enrichment broth Nalidixic acid acid 30 mg/liter | 1.86 | 1.67 | 1.37 | 0.79 | 0.39 |
| L. monocytogenes ATCC 19116 nonselective nutrient broth | 2.31 | 1.50 | 0.95 | 0.58 | 0.35 |
| pre-enrichment broth Nalidixic acid 30 mg/liter | 2.49 | 1.28 | 0.89 | 0.63 | 0.44 |

)$^a$ The Listeria monocytogenes cells were injured by subjecting cells to 54° C. for 30 to 45 minutes prior to adding to a nonselective nutrient broth (control) and the pre-enrichment broth containing nalidixic acid at 30 mg/liter.
)$^b$ Log$_{10}$ number of Listeria monocytogenes cells/ml injured. Incubation of cells in the broth the injured cells will repair. After 10 hours, the injured Listeria monocytogenes cells initiated growth indicating the end of the repair period.

Example 5

Inoculation, Preparation and Efficacy of the Selective Enrichment Broth

In this example, the selective enrichment broth prevented the growth of particular bacteria except for the genus Listeria and incorporated a fluorogenic PI-PLC substrate to yield a presumptive positive response by Listeria monocytogenes and Listeria ivanovii displayed by a fluorescence (detected by a hand held UV fluorometer—366 nm) after incubation at 35° C. for 24 to 48 hours.

Other bacteria containing the PI-PLC enzyme are prevented from growing in the selective enrichment broth yielding an excellent specificity for Listeria monocytogenes in a fluorescent tube after incubation.

Among the Listeria species, only the pathogenic Listeria monocytogenes and Listeria ivanovii species can produce a fluorescence in the Selective Enrichment Broth after incubation as shown in Table 5.

| | |
|---|---|
| Proteose Peptone (ex Difco) | 4.0 grams/liter |
| Yeast Extract (ex Difco) | 7.0 grams/liter |
| Tryotone (ex Difco) | 10.0 grams/liter |
| Casamino acids (ex Difco) | 6.2 grams/liter |
| Glucose | 3.1 grams/iiter |
| Potassium Phosphate (dibasic) anhydrous (ex Sigma) | 4.5 grams/liter |
| Lithium chloride (ex Sigma) | 7.5 grams/liter |

All ingredients were dissolved in 1 liter of water (distilled or deionized), dispensed in 10 ml volumes and autoclaved at 121° C. for 15 minutes.

| Supplements: | |
|---|---|
| Bovine Albumin (Bayer 82-067) | 4.0 grams/liter |
| Ceftazidime Pentahydrate (ex Glaxo Wellcome) | 0.035 grams/liter |
| 4-Methylumbelliferyl myo-mositol-1-phosphate, N-methylmorpholine salt | 0.4 grams/liter |

The supplements were dissolved aseptically in a total of 30 ml of sterile distilled or deionized water and added (0.3 ml per 10 ml of basal medium) aseptically to above medium.

The stability of the Selective Enrichment at 4° C. in the dark was 4 weeks.

TABLE 5

Fluorogenic response of various Listeria species in the Selective enrichment Broth after incubation at 35° C. for 24 hours

| Listeria species | Fluorogenic response |
|---|---|
| Listeria monocytogenes 4 b | bright fluorescence with the fiuorescence partially up the test tube |
| Listeria monocytogenes 1/2 b | bright fluorescence with the fluorescence partially up the test tube |
| Listeria monocytogenes ATCC 43249 | Bright fluorescence with the fluorescence partially up the test tube |
| Listeria monocytogenes 3 a | Bright fluorescence with the fluorescence partially up the test tube |
| Listeria innocua | No fluorescence; same as the uninoculated control tube containing the selective enrichment broth |

Example 6

Preparation, Inoculation and Efficacy of Selective Plating Medium

This example illustrates preparation, inoculation, efficacy, and stability of a solid plating medium according to the invention.

Composition of Plating Agar:

| | |
|---|---|
| Proteose Peptone (ex Difco) | 3.0 grams/liter |
| Tryptone (ex Difco) | 12.0 grams/liter |
| Casamino acids (ex Difco) | 6.0 grams/liter |
| Lab Lemco Powder (ex Oxoid) | 5.0 grams/liter |
| Glucose | 2.5 grams/liter |
| Yeast Extract (ex Difco) | 8.0 grams/liter |
| Potassium phosphate (dibasic) | 4.5 grams/liter |
| Lithium chloride (ex Sigma) | 4.5 grams/liter |
| Agar (ex Difco) | 15.0 grams/liter |

All ingredients were dissolved in 970 ml of water (distilled or deionized) and autoclaved at 121° C. for 15 minutes.

Supplements:

| | |
|---|---|
| Bovine albumin (Bayer 82-067) | 3.0 grams/liter |
| Ceftazidime pentahydrate (ex Glaxo Wellcome) | 0.035 grams/liter |
| 5-Bromo-4-chloro-3-indoxyl myo-inositoi-1-phosphate, ammonium salt | 0.3 grams/liter |

The supplements were dissolved aseptically in a total of 30 ml of sterile distilled or deionized water and added aseptically to above medium after cooling in a water bath to 50–55° C.

The complete medium was poured into petri dishes and the surface dried by storing the plates at room temperature for 2 days in the dark. Excess plates can be stored at 4° C. in the dark for up to 12 weeks and still function as freshly poured plates.

The plating medium was inoculated by using a loopful liquid from a fluorescent selective enrichment broth and streaking onto the agar to facilitate the isolation of *Listeria monocytogenes* colonies.

The plating medium was incubated at 35° C. for 48 hours. After incubation, colonies displaying the following characteristics were considered presumptive *Listeria monocytogenes* and required further testing using standard *Listeria monocytogenes* identifying methods: turquoise to blue color, convexed, 1.0–2.5 mm in diameter without or with a turquoise to blue halo surrounding the colony.

Table 6 shows the colonial characteristics of a variety of bacteria on the selective/differential plating medium after incubation.

The turquoise to blue color of the *Listeria monocytogenes* colony indicated the presence of the PI-PLC enzyme by forming the deeply colored 5,5'-dibromo-4,4'-dichloro-indigo water insoluble complex which was retained within the colony and did not diffuse into the medium. This insoluble complex makes it more suitable in a solid medium than in a broth.

TABLE 6

| Bacterial strains | Number of Strains | Colonial morphology |
|---|---|---|
| *Listeria monocytogenes* | 68 | turquoise colored convex coiony, 1.0–2.5 mm in diameter. With or without turquoise halo. |
| *Listeria ivanovii* | 3 | turquoise colored convex colony,1.0–1.5 mm in diameter. With a dark turquoise halo. |
| *Listeria welshimeri* | 3 | white colored convex colony, 2.0 mm in diameter. No precipitate or halo surrounding the colony. |
| *Listeria grayi* | 1 | white colored convex colony, 1.0 mm in diameter. No precipitate or halo. |
| *Listeria innocua* | 6 | white colored convex colony, 1.0–2.0 mm in diameter. No precipitate or halo. |
| *Listeria seeligeri* | 1 | white colored convex colony, 1.0–2.0 mm in diameter. No precipitate or halo. |
| *Bacillus thuringiensis* | 3 | large flat colony with granular turquoise center surrounded by a lighter turquoise ring of target-like shape. a |
| *Bacillus cereus* | 2 | No growth. |
| *Staphylococcus aureus* | 3 | No growth. |
| *Staphylococcus epidermidis* | 2 | No growth. |
| *Enterccoccus feacalis* | 2 | White pinpoint colony. <1 mm in diameter. No surrounding precipitate. |
| *Enterococcus faecium* | 4 | No growth for 2 strains. Scattered white pinpoint colony <1 mm diameter for 2 strains. |
| *Enterococcus avium* | 3 | No growth. |
| *Lactobacillus plantarum* | 1 | No growth. |
| *Lactococcus lactis* | 1 | No growth. |
| Gram negative species, mainly members of the Pseudomcnadaceae, Neisseriaceae, Enterobacteriaceae, and Vibrionaceae family. | 17 | No growth. |

It should be noted that while the above examples are concerned with MeU-phos-inositol and X-phos-inositol, the preferred substrates of formula (I) and (IV), respectively, it is apparent from the general disclosures above that very similar results will be obtained with other substrates of formula (I) and (IV), respectively. Thus, various modifications of the examples given above will be apparent.

Generally, the invention provides for safe, sensitive and commercially viable detection of potentially pathogenic bacterial activity of such microbes as *Staphylococcus aureus* and various *Listeria monocytogenes* and *Listeria ivanovii* strains in potentially infected materials including physiological samples or consumable goods such as foods and beverages. The scope of the invention is to be construed on the basis of the following claim.

What is claimed is:

1. A potentially fluorogenic compound of formula (I)

(I)

in which $R^1, R^2, R^3, R^4$ and $R^5$ are independently selected from the group consisting of hydrogen and chromogenic substituents, and X is selected from the group consisting of: hydroxyl; $OR^6$ wherein $R^6$ is selected from the group consisting of $C_1-C_4$ alkyl; and $O^{-Me+}$ wherein $Me^-$ is a cation derived from an organic or inorganic base.

2. The compound of claim 1 wherein said base is selected from the group consisting of sodium hydroxide, potassium hydroxide, lithium hydroxide, ammonium hydroxide, diethylamine, triethylamine, tetramethylammonium hydroxide, tetra-ethylammonium hydroxide, cyclohexylamine, pyridine, piperidine, pyrrolidine, morpholine, N-methyl-morpholine, N-ethyl-morpholine and p-toluidine.

3. The compound of claim 1 wherein said chromogenic substituents are selected from the group consisting of $C_1-C_4$ alkyl optionally containing an oxygen atom in the alkyl chain; $C_1-C_4$ alkoxy; nitro; carboxy, $C_1-C_4$ carboxyalkyl, and cyano, wherein any of said alkyl groups may include one or more halogen atoms as substituents.

4. The compound of claim 1 wherein $R^3$ is a lower alkyl optionally containing one or more halogen atoms, X is hydroxyl, and $R^1, R^2, R^4$ and $R^5$ are hydrogen atoms; and the salts of said compound with an organic or inorganic base.

5. 4-Methylumbelliferyl myo-inositol-1-phosphate and the salts thereof with an organic or inorganic base.

6. A method of detecting microbial activity in a sample; said method comprising the steps of (i) combining said sample with a compound of formula (I) as claimed in claim 1; and (ii) inspecting said sample combined with said formula (I) compound or said salt thereof by fluoro-scopic means.

7. The method of claim 6 wherein said sample is treated with a pre-enrichment broth to increase said activity prior to said step (A).

8. The method of claim 7 wherein said pre-enrichment broth is selective for microbes exhibiting said activity.

9. The method of claim 6 for use as a screening test in the detection of bacteria of the group comprising Listeria, Staphylococcus and Clostridium.

10. A method of identifying a microorganism of interest which is capable of producing a phosphatidyl-inositol-specific phospholipase C enzyme comprising the steps of:

(A) providing a test sample suspected of containing said microorganism;

(B) submitting said test sample to a pre-enrichment step;

(C) combining a portion, at least, of the product obtained in step (B) with a compound as defined in any of claims 1–5 to provide a screening sample which exhibits a positive fluoroscopic response when said microorganism is present in said test sample;

(D) transferring a portion, at least, of the product obtained in step (B)—if said screening sample exhibits a positive fluoroscopic response—to a medium suitable for culturing said microorganism, said medium containing at least one compound capable of producing a color when exposed to said microorganism;

(E) cultivating said medium with said transferred portion for developing at least one colony exhibiting said color; and (F) recovering a portion, at least, of said colored colony for final identification.

11. The method of claim 10 wherein said at least one compound capable of a producing color when exposed to said microorganism is a compound of formula IV (IV)

wherein $R^{10}$ is selected from the group consisting of hydrogen and $C_{1-4}$ alkyl, such a methyl, ethyl, propyl or butyl, and $R^6, p^7, R^8$, and $P^9$ are selected from the group consisting of hydrogen and chromogenic substituents; or a salt of said formula IV compound with an organic or inorganic base and sulphonyl.

12. The method of claim 11 wherein $R^6$ and $R^7$ are selected from chlorine and bromine; $R^8$ and $R^9$ are hydrogen and $R^{10}$ is hydrogen and/or wherein said formula IV compound is in the form of a salt with an organic or inorganic base.

13. The method of claim 10 wherein said microorganisms of interest are bacteria from the group comprising Listeria, Staphylococcus and Clostridium.

14. A substrate for detecting a phosphatidyl-inositol-specific phospholipase C enzyme as an indication of bacterial activity; said substrate containing at least one compound as defined in claim 1.

15. A kit for detecting a phosphatidyl-inositol-specific phospholipase C enzyme as an indication of bacterial activity, said kit including at least one compound of formula I as defined in claims 1–5.

16. The kit of claim 15 further comprising at least one compound of formula IV as defined in any of claim 11.

17. A method of producing a compound as claimed in claim 1 characterized by converting a compound of formula IIIA into the compound of formula IIIB according to the reaction (IIIA)

-continued (IIIB)

in which Ins represents inositol and G represents a HO-protecting group on each hydroxyl of the inositol except the 1-hydroxy, and wherein X and $R^1$–$R^5$ have the meaning indicated in claim 1; removing the HO-protecting groups; and optionally forming a salt by reaction with an organic or inorganic base when X represents hydroxyl.

18. The compound of claim 3 wherein said halo-substituted alkyl group is a trifluoromethyl group.

* * * * *